United States Patent [19]

Erbe et al.

[11] Patent Number: 5,622,551
[45] Date of Patent: Apr. 22, 1997

[54] CHEMICALLY DERIVED LEUCITE

[75] Inventors: Erik M. Erbe, Stillwater; Ronald S. Sapieszko, Woodbury, both of Minn.

[73] Assignee: Minnesota Mining and Manufacturing Company, St. Paul, Minn.

[21] Appl. No.: 536,073

[22] Filed: Sep. 29, 1995

Related U.S. Application Data

[63] Continuation of Ser. No. 338,278, Nov. 14, 1994, abandoned, which is a continuation of Ser. No. 145,493, Oct. 29, 1993, abandoned.

[51] Int. Cl.$^6$ ................................................. C09K 3/00
[52] U.S. Cl. ........................ 106/35; 423/328.1; 501/6; 501/12; 501/32
[58] Field of Search .................. 106/35; 501/101, 501/125, 128, 153, 154, 6, 12, 21, 32, 141, 17, 16; 423/328.1

[56] References Cited

U.S. PATENT DOCUMENTS

| | | |
|---|---|---|
| 3,052,982 | 9/1962 | Weinstein et al. . |
| 3,052,983 | 9/1962 | Weinstein et al. . |
| 3,464,837 | 9/1969 | McLean et al. . |
| 3,653,865 | 4/1972 | Megles . |
| 4,101,330 | 7/1978 | Burk et al. ........................ 106/35 |
| 4,158,641 | 6/1979 | Miyai et al. . |
| 4,431,451 | 2/1984 | Mabie et al. . |
| 4,445,383 | 6/1984 | Panzera . |
| 4,455,383 | 6/1984 | Panzera . |
| 4,604,059 | 8/1986 | Klaus et al. . |
| 4,604,366 | 8/1986 | Kaciez et al. . |
| 4,798,536 | 1/1989 | Katz . |
| 5,071,801 | 12/1991 | Bedard et al. . |
| 5,096,862 | 3/1992 | Mathers et al. . |

FOREIGN PATENT DOCUMENTS

| | | |
|---|---|---|
| 0124298 | 7/1984 | European Pat. Off. . |
| 0272745 | 6/1988 | European Pat. Off. . |
| 0543065 | 5/1993 | European Pat. Off. . |
| 60-33254 | 2/1985 | Japan . |
| 0033254 | 2/1985 | Japan . |
| 5-43312 | 2/1993 | Japan . |

OTHER PUBLICATIONS

*Introduction to the Principles of Ceramic Processing*, Reed, (1988) pp. 124–127.

Primary Examiner—Paul Marcantoni
Attorney, Agent, or Firm—Gary L. Griswold; Walter N. Kirn; Dale A. Bjorkman

[57] ABSTRACT

Chemically derived leucite is claimed. The chemically derived leucite is obtained from a stable dispersion of a potassia precursor, an alumina precursor and a silica precursor having a specified dry weight solids content. Chemically derived tetragonal leucite is particularly useful as a component of a dental porcelain.

37 Claims, 1 Drawing Sheet

CHEMICALLY DERIVED LEUCITE

This a continuation of application Ser. No. 08/338,278, filed Nov. 14, 1994, abandoned, which is a continuation of Ser. No. 08/145,493, filed Oct. 29, 1993, abandoned.

BACKGROUND OF THE INVENTION

1. Field of the Invention

This invention relates to leucite chemically derived from a stable dispersion of a potassia precursor, an alumina precursor and a silica precursor. More specifically, it relates to congruently crystallized tetragonal leucite useful as a component of a dental porcelain. A process of preparing chemically derived leucite is also described.

2. Description of the Background Art

Porcelains are widely used in the dental industry as tooth restorations. A common type of restoration is a metal-based restoration, wherein several layers of porcelain are sequentially fused to a metal framework generally referred to as a "coping". These dental porcelains are typically blends of many frits or components. Various frits are combined to achieve certain desirable properties, such as color, strength, translucency, shock resistance and coefficient of thermal expansion ("CTE").

Conventionally, dental porcelains are made by admixing a glass frit (having a low CTE and optionally containing pigments and fluorescent additives) and a leucite-containing frit (having a high CTE) in appropriate ratios. The leucite-containing frit is derived by processing (i.e., firing) naturally occurring minerals such as potash feldspar ($KAlSi_3O_8$), albite feldspar ($NaAlSi_3O_8$) or nepheline syenite ($NaKAlSi_3O_8$). In order to be useful as a component in porcelain, these feldspathic minerals are typically purified to remove contaminants, especially undesirable quantities of transition metal cations such as iron, chromium, nickel and manganese.

An important criterion in selecting a dental porcelain is the degree to which the CTE of the porcelain and that of the substrate or coping match. It is generally desirable to utilize a dental porcelain with a CTE slightly less than the CTE of the metal coping such that, upon cooling, the porcelain is placed in compression. Another important criterion in selecting a dental porcelain is translucency, which is directly proportional to the amount of crystalline phase in the porcelain. The degree of light transmission through a porcelain is directly dependent on the difference in refractive indices of the respective components, the volume fraction crystallized ("Vc") of leucite and the amount of leucite in the final composition.

U.S. Pat. Nos. 3,052,982 and 3,052,983 to Weinstein disclose mixing glass and glass-ceramic frits of different composition and different CTE. The resultant porcelains exhibited an intermediate CTE and the requisite mechanical integrity. By combining frits of various melting temperature, composition, and CTE characteristics, the user could tailor the CTE of the porcelain to match that of the desired metal base. After processing, the porcelain consisted of a glassy matrix with integrated tetragonal leucite.

It was recognized very early in the dental porcelain industry that tetragonal leucite, in particular, was a critical component in glass-ceramics to obtain the correct thermal expansion matching. Furthermore, its presence in dental porcelain was recognized as advantageous because it could impart higher strength, greater durability and the desired translucency to the final porcelain. Therefore, considerable effort in the field of dental porcelains has been directed to mixing as many as seven frits, each processed under different conditions, to obtain a final fired porcelain containing some tetragonal leucite phase and exhibiting the overall desired chemical, mechanical and aesthetic characteristics.

U.S. Pat. No. 3,464,837 to McLean et al. discloses a dental material formed from naturally occurring materials such as refractory oxides and feldspar. The material is said to exhibit superior mechanical strength.

U.S. Pat. No. 4,604,059 to Klaus et al. discloses blends of two different glass frits with two different glass-ceramic powders in varying ratios. The resultant blends exhibit thermal expansion coefficients varying from about $10 \times 10^{-6}/°$ C. to about $19 \times 10^{-6}/°$ C. The mineral feldspar is one of the components.

Work has also been directed to finding a single frit which would meet the thermal expansion coefficient requirements for dental porcelains. For example, U.S. Pat. No. 4,455,383 to Panzera discloses mixtures containing silica, alumina, potassia, a fluxing agent and other metal oxides to obtain a frit having a fired CTE of about $12-14 \times 10^{-6}/°$ C. With proper heat treatment, the crystalline phase leucite was formed. Rouf et al. in *Trans. Br. Ceram. Soc.* (1978), Vol. 77, p. 36 describe work directed to controlling the crystallization of aluminosilicate glasses by means of different nucleating agents. The goal was to produce a glass-ceramic with the desired crystalline phase.

U.S. Pat. No. 4,798,536 to Katz discloses the addition of potassium salts to feldspar to produce porcelains having a greater amount of leucite phase and improved strength.

U.S. Pat. No. 5,071,801 to Bedard et al. discloses a process of ion exchanging a zeolite to obtain a ceramic article having tetragonal leucite as the principle crystalline phase. Thermal expansion of the material is controlled by introduction of a pollucite ($CsAlSi_2O_6$) phase into the leucite.

Limitations of conventional processing methods include the necessity of attaining high fusion temperatures as well as inhomogeneity of the processed powders. In contrast, sol-gel chemical ceramic processes are recognized as a way to obtain high purity, homogeneous ceramic compositions which require lower fusion temperatures for densification. These methods have been applied to the production of multicomponent feldspathic glasses. Jones et al. in *J. Canadian Ceramic Society* (1986), Vol. 55, p. 42–49 describe the cohydrolysis of aluminum alkoxides and ethyl orthosilicates in the synthesis of multicomponent feldspathic glasses using alkaline alkoxides and colloidal solutions of silica and alumina. For example, Rizkalla et al. in *Br. Ceram. Trans. J.* (1991), Vol. 90, p. 81–84 report the use of metal alkoxide hydrolysis to produce eight-component feldspathic glasses. These methods require the use of fluxing agents, nucleating agents and grain growth inhibitors to obtain a glass with the desired characteristics.

C. P. Mabie and coworkers have reported on a gel route of preparing low fusing dental porcelain frits in *J. Biomedical Materials Research* (1983), Vol.17, p. 691–713. Chloride stabilized alumina and alumina-silica sols were used. U.S. Pat. No. 4,431,451 to Mabie et al. discloses a dental porcelain frit prepared by a gel route.

Emu et al in JP 5-43312 describe the formation of anorthite ($CaOAl_2O_3 2SiO_2$) feldspathic powders for low cost substrates with improved purity and lower sintering temperatures. Emu utilized a boehmite (AlOOH) sol, a colloidal silica sol and a calcium salt which were gelled by boric acid and sintered at temperatures of 900°–1200° C.

Typically, leucite is incongruently crystallized (i.e., the stoichiometric composition of the amorphous matrix differs from that of the crystalline phase which derives from it) by the heat treatment of a precursor (i.e., antecedent) glassy matrix containing potassia, alumina, silica and other components such as alkali fluxes, nucleating agents and grain growth inhibitors. Feldspathic minerals, which include potash feldspar, albite feldspar, and nepheline syenite, usually provide the requisite precursor oxide matrix. To crystallize a significant percentage of leucite from a potassium aluminosilicate mineral, a minimum of about 12 weight % potassia is required. These conventional processes require additional alkalies (e.g., $Li_2O$, $Na_2O$, or $K_2O$) as fluxing agents to reduce the liquidus temperature of the parent mineral source. Even when fluxing agents are used, the firing of feldspathic minerals typically exceeds 1100° C. and usually requires temperatures in excess of 1200° C. for several hours. Additionally, nucleating agents (e.g., CaO, $ZrO_2$, $TiO_2$) are generally added to initiate incongruent crystallization of leucite. The glass-ceramics obtained by this method generally contain less than about 40 volume % tetragonal leucite with the residual glass matrix varying in composition based on the amount of leucite crystallized.

Leucite, which has the chemical composition $K_2OAl_2O_3.4SiO_2$, can manifest either a tetragonal or cubic crystalline phase. High temperature frit formation can produce varying amounts of the cubic phase of leucite, a metastable phase which usually converts to the tetragonal phase upon cooling. The cubic phase has a low CTE (approximately $10-12\times10^{-6}/°$ C.) and its presence in dental porcelain is particularly undesirable because of the low CTE and the volume expansion accompanying the cubic to tetragonal transition upon cooling during preparation of a porcelain fused to metal restoration. The tetragonal phase, on the other hand, has a high CTE (approximately $22-30\times10^{-6}/°$ C.) and is very desirable for admixture with glasses which generally have a low CTE and for bonding with metal substrates having a high CTE. Therefore, much work has been directed to controlling the formation of tetragonal leucite and its subsequent phase purity in porcelains, generally by controlling the time-temperature conditions under which the porcelain is processed.

The importance of using tetragonal leucite has been recognized in the dental porcelain art for some time. However, none of the aforementioned processes provides chemically derived leucite or congruently crystallized leucite.

SUMMARY OF THE INVENTION

The present invention in one embodiment is chemically derived leucite formed from a stable dispersion of a potassia precursor, an alumina precursor and a silica precursor, wherein the dry weight solids content after firing comprises on a theoretical basis, 12 to 30 weight % $K_2O$, 8 to 30 weight % $Al_2O_3$ and 45 to 73 weight % $SiO_2$. The resultant leucite composition is substantially free of processing aids.

Another embodiment of the invention is congruently crystallized tetragonal leucite consisting essentially of 21.6 weight % $K_2O$, 23.4 weight % $Al_2O_3$ and 55.0 weight % $SiO_2$. This composition is particularly useful for adjusting certain properties of dental porcelains.

Yet another embodiment is tetragonal leucite formed by a process comprising the steps of a) mixing a potassia precursor, an alumina precursor and a silica precursor to form a stable dispersion wherein a composition is formed having a dry weight solids content after firing of 12 to 30 weight % $K_2O$, 8 to 30 weight % $Al_2O_3$ and 45 to 73 weight % $SiO_2$; b) drying the composition formed by step a); c) calcining the composition formed by step b); and d) firing the composition formed by step c). Another embodiment is chemically derived fluorescent tetragonal leucite. Another embodiment is chemically derived pigmented tetragonal leucite. Another embodiment is chemically derived $K_2O$—$Al_2O_3$—$SiO_2$ glasses within the previously specified compositional range. Another embodiment includes other chemically derived $K_2O$—$Al_2O_3$—$SiO_2$ crystal phases where a portion of the potassium or aluminum is substituted by other alkali, alkaline earth, rare earth, and/or transition metal oxides.

Porcelains prepared from the chemically derived leucite of the invention can be used as coatings for metal articles, metal-ceramic seals, catalyst supports, integrated circuit components, and heat exchangers. In the dental industry, these porcelains can be used to make inlays, onlays and prosthetic devices such as crowns, bridges and veneers.

DETAILED DESCRIPTION

Figure 1:
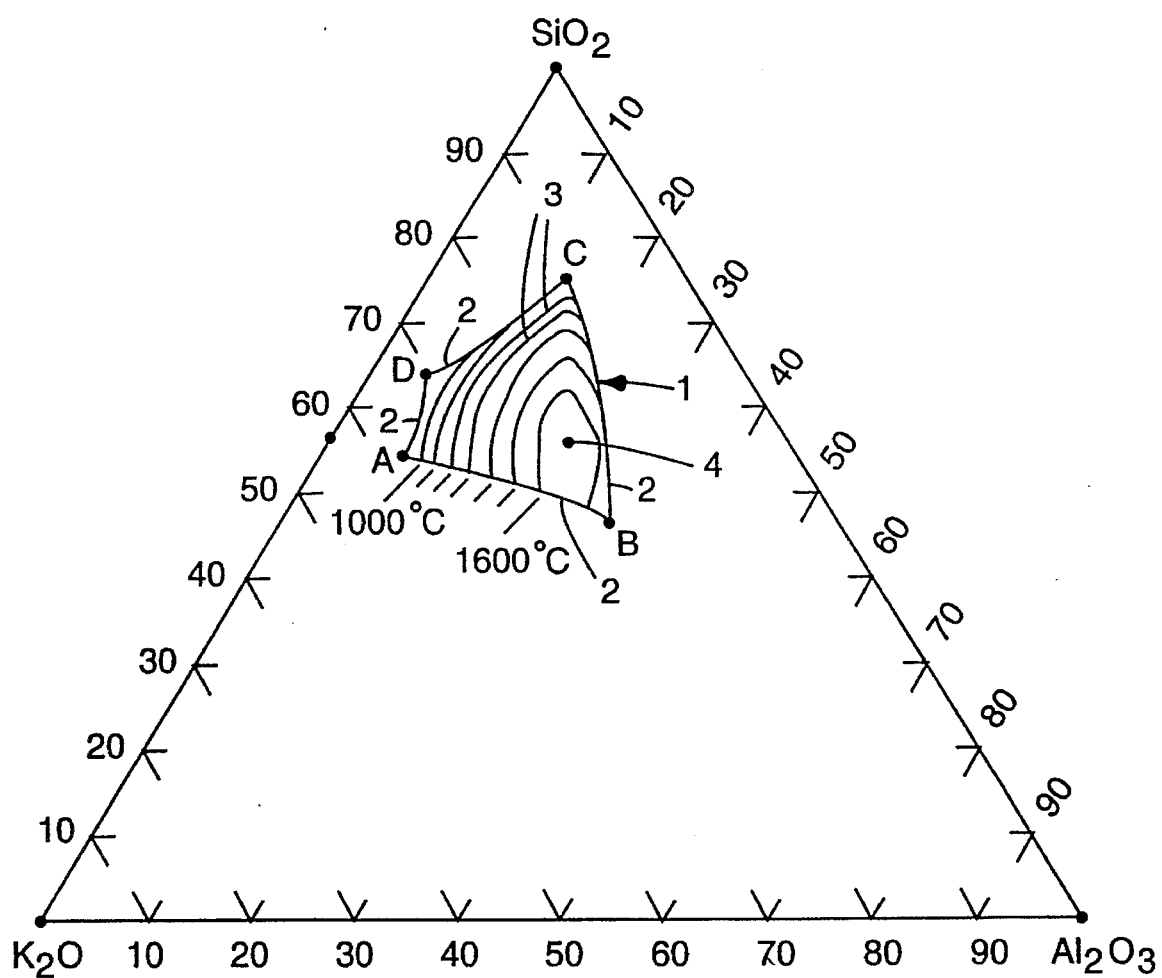
FIG. 1 is a ternary phase equilibrium diagram of the compositional and phase relationships of $K_2O$, $Al_2O_3$ and $SiO_2$ as a function of temperature at one atmosphere pressure. The leucite phase field is outlined and the point corresponding to the stoichiometric composition of the compound leucite is identified.

The chemically derived leucite of the present invention is substantially free of processing aids and can be congruently crystallized. As used herein, the term "porcelain" means the ceramic materials used to formulate inlays, onlays and prosthetic dental appliances such as veneers, crowns and bridges with or without a metal coping. The phrase "chemically derived leucite" means leucite synthesized from its chemical constituents in a dispersion (i.e., neither naturally occurring leucite per se nor leucite directly derived from mineral sources such as feldspar). The chemically derived leucite of the invention can be substantially free of processing aids and undesirable quantities of transition metal cations, particularly iron and chromium. However, these processing aids and transition metal cations are easily incorporated into said dispersions and can be used to adjust the composition and properties of the resultant materials.

The phrase "congruent crystallization" means that the amorphous matrix has the same stoichiometric composition as the crystalline phase which derives from it. The terms "sol", "colloid" or "dispersion" as used herein mean a uniform suspension of finely divided particles (i.e., average particle size usually between about $5\times10^{-4}$ and about $5\times10^{-1}$ micrometer) in a liquid medium. The term "stable" as used herein means that the small particles of the dispersion remain uniformly distributed throughout a sample for at least one hour at 25° C. More preferably the dispersion is stable at 25° C. for at least one day and most preferably for at least one week. The word "compatible" means that a solution or sol, when added to another solution or sol, does not cause gelation, flocculation, precipitation or phase separation for at least one hour from the time of addition. The term "precursor" means a salt, a solution derived from a salt, or a sol from which a subsequent oxide composition is obtained. The phrase "processing aids" means components such as fluxing, nucleating or fusing materials that typically are inorganic oxides and are added to aid in firing and to control grain growth or particle size of the final composition.

"Nucleating agent" as used herein refers to an externally introduced leucite crystal growth site. The term "nucleating material" as used herein refers to a nucleating agent or a precursor thereof. The word "additives" means components that are added to the dispersion to facilitate processing or handling properties of the dispersion or formation of the final product (e.g., powder particle size, fiber or bubble formation), but are not present in the final product (e.g., eliminated in drying, calcining or firing). The word "firing" means heating to a temperature sufficient to initiate crystallization of leucite as determined by x-ray crystallography or to convert a salt intermediate to a vitreous state. Preferably, at least 40% of the theoretical maximum of leucite is crystallized. More preferably, at least about 75% of the theoretical maximum of crystallized leucite is formed, and most preferably, at least about 95% of the theoretical maximum is formed. However, when the word firing is used in reference to porcelain fabrication, it means to heat the porcelain to a temperature and for a time sufficient for fusion or maturation of the components.

A process has been discovered wherein a potassia precursor, an alumina precursor, and a silica precursor are mixed together to form a stable dispersion, which is dried, calcined and crystallized by firing to form chemically derived leucite. The leucite thus produced can be substantially free of impurities such as undesirable quantities of transition metal cations (commonly found in naturally occurring leucite or leucite derived from mineral sources) and processing aids. By controlling the stoichiometry of the mixture the amorphous matrix can have the same chemical composition as the crystalline phase derived from it. Optionally, other components can be added to the dispersion to adjust the final composition and properties of the alkali aluminosilicate materials derived from the dispersion. The components include one or more of the following: alkali (Li, Na, Rb, Cs) alkaline earth (Mg, Ca, Sr, Ba), transition metal (Ti, V, Cr, Mn, Fe, Co, Ni, Cu, Zn, Zr, Cd, Hg, Pt, Ag), and/or rare earth (Y, La, Ce, Pr, Nd, Sm, Eu, Gd, Tb, Dy, Ho, Er, Tm, Yb, Th) oxides. It is also possible to incorporate other compatible components such as glass forming oxides (e.g. $B_2O_3$, $P_2O_5$), halides (F, Cl, Br, I), chalcogenides (S, Se, Te), and/or Group V elements (P, As, Sb, Bi) provided the salts of these components have sufficient water solubility in the dispersion and do not compromise the dispersion stability. By controlling the stoichiometry of the reaction mixture, the amorphous matrix can have the same chemical composition as the crystalline leucite phase which is derived from it.

The ternary phase equilibrium diagram in FIG. 1 represents all the known compositional and phase relationships of $K_2O$, $Al_2O_3$ and $SiO_2$ as a function of temperature at one atmosphere pressure (modified from J. F. Schairer and N. L. Bowen, *Am. J. Sci.*, (1947), Vol. 245, p. 199, 201). All the crystallization processes are time-temperature dependent. The diagram reflects the lowest energy, stable, equilibrium state at a given temperature.

Compounds (e.g., $K_2O.2SiO_2$) within a binary system of the apex components are marked on the sides of the equilateral triangle next to the point representing that weight % composition. The leucite phase field 1 is enclosed within phase boundary lines 2 and denotes the region of the phase diagram within which the first crystalline solid to be formed on cooling has the chemical composition of leucite. The contour lines 3 within the phase boundary lines 2 are the temperature isotherms which denote the temperature at which a liquid having the composition of leucite will first appear. Upon crystallization, the first crystalline phase to form from any composition selected within the leucite phase field will be leucite.

Referring now to the drawing, the composition of starting materials within the phase field 1 having a boundary defined by A, B, C, and D and including the boundary lines A-B, B-C, C-D, and D-A consists essentially of 12–30 weight % $K_2O$, 8–30 weight % $Al_2O_3$, and 45–73 weight % $SiO_2$ and comprises amorphous and/or crystalline phases. The amorphous matrix has a stoichiometry congruent with leucite only at point 4 where there is present 21.6 weight % $K_2O$, 23.4 weight % $Al_2O_3$, and 55.0 weight % $SiO_2$. Upon congruent crystallization of the matrix at point 4, up to 100 volume percent of the composition can be in the crystalline tetragonal phase. The amount of the crystalline phase is controlled by both time and temperature.

Three components are mixed together in the process of this invention to form chemically derived leucite. The components are a potassia precursor, an alumina precursor and a silica precursor.

The first component is a potassia precursor. Preferred precursors are derived from a potassium salt. Preferred potassium salts include acetates, nitrates, chlorides, carboxylates, sulfates, perchlorates and mixtures thereof. It is preferred to use potassium acetate with a small amount of another potassium salt. Most preferred is the use of potassium acetate alone. While not being bound by theory, acetate salts are preferred because it is believed that the acetate anion promotes stabilization of the alumina precursor:silica precursor mixture for the greatest amount of time. This is believed to be true because acetate salts generally have high water solubility and tend to buffer the solution pH in a mildly acidic range from pH 4.5 to 5.5 Additionally, in the process of calcining and firing to give a powder, acetate generally gives the cleanest and most controllable burn-out (i.e., no carbon or nitrogen residues remain). Some salts, such as, for example, chloride, produce stable dispersions, but may leave undesirable residues in a final fired product. Other salts such as, for example, nitrate generally undergo exothermic decomposition on firing making processing more difficult.

The second component is an alumina precursor. Preferred precursor are derived from an aluminum salt. Preferred aluminum salts include basic aluminum carboxylates, basic aluminum nitrates and partially hydrolyzed aluminum alkoxides. It is preferred to use aluminum formoacetate ("AFA") with a small amount of another salt. Most preferred is the use of AFA alone due to the high equivalent content of alumina that can be attained. AFA can be prepared according to the procedure described in Example 1 of U.S. Pat. No. 4,798,814 (Everitt, et al.) by digesting aluminum metal in a mixture of formic acid and acetic acid to form a clear solution. The ratio of total carboxylic acid to aluminum is about 1:1; the solution is equivalent to about 8 to 10 weight percent alumina.

Although AFA is the preferred alumina precursor, mixtures of AFA and other alumina precursors (e.g., other basic aluminum carboxylates, basic aluminum nitrates, partially hydrolyzed aluminum alkoxides, or other aluminum salts and complexes) are useful in the practice of this invention. Suitable alumina precursors are water soluble basic aluminum salts. Particularly useful alumina precursors are basic aluminum carboxylates of the general formula $Al(OH)_y(carboxylate)_{3-y}$, where y is between 1 and 2, preferably between 1 and 1.5, and the carboxylate counterion is selected from the group consisting of formate, acetate, propionate, and oxalate or combinations of these carboxylates. These carboxylates can be prepared by digesting aluminum metal in a solution of the carboxylic acid as described in U.S. Pat. No. 3,957,598. Basic aluminum nitrates have the general formula $Al(OH)_z(NO_3)_{3-z}$, where z is between about 0.5 to 2.5 and can be prepared by digesting aluminum metal in a nitric acid solution as described in U.S. Pat. No. 3,340,205. The aforementioned basic aluminum salts can also be prepared by partially neutralizing an aluminum salt with a base.

The third component is a silica precursor. Preferred silica precursors are silica sources that can be fired to form residual $SiO_2$, such as aqueous silica sols, solutions of alkoxysilanes or siloxane polymers and oligomers. Suitable silica sols are commercially available under the trade designation Ludox, from E. I. dupont de Nemours (Wilmington, Del.). Other suitable silica sols are available from Nalco Chemical Co. (Naperville, Ill.) under the trade designations Nalco 1034A, Nalco 1042, Nalco 2326, and Nalco 2327. Preferred silica sols include Nalco 1034A and Nalco 1042, which contain approximately 34% by weight silica solids, and have a pH of no greater than 4.0.

The potassia precursor, the alumina precursor, and the silica precursor are mixed together. Although it is believed that the components can be mixed in any order, they should be added together in a manner such that a stable dispersion is obtained. Salts or blends of salts are preferably added as aqueous solutions since the addition of solids would tend to cause flocculation of the dispersion due to localized concentration gradients during dissolution of the salt. Although it is preferred that the dispersion remain stable and homogeneous, a non-homogeneous dispersion may be utilized if it is redispersed by, for example, vigorous stirring or ultrasonication so as to avoid large scale segregation of the components.

It is preferred to add the alumina precursor to the potassia precursor with moderate stirring and, subsequently, to add the silica precursor to the potassia precursor:alumina precursor mixture with rapid stirring. Although rapid stirring tends to promote the temporary formation of a foam layer due to entrainment of air, this foam layer subsides after about 15 minutes to reveal a weakly turbid, blue-white colloid. The weak turbidity is acceptable and indicates a minor degree of aggregative particle growth. The final dispersion, which will reduce to the final oxide composition of leucite on firing, is preferably stable at room temperature for at least one year.

The stability of the mixture is a function of the pH, the ionic strength, the temperature, the solubility of the individual components, and the size and charge of the cations and anions. The dilution (i.e., ratio of salts and sol to water) also affects the stability of the dispersion. Generally, it is convenient to use a dispersion having an equivalent oxide solids content (i.e., calculated based on the formula for the final oxide phase) of about 20 weight %, although the solids content may range up to about 24 weight % or more. The dispersion preferably has a pH less than 7, more preferably of 3–6 and most preferably of 5–6.

Small amounts of additives may be present in the dispersion. Additives are components that are added to the dispersion to facilitate processing or handling properties of the dispersion or formation of the final product, but are not present in the final product. Examples of such additives include fiberizers, drying control additives, film forming agents, surfactants, dopants (e.g., inorganic pigments), plasticizers, monomers, and polymers, all of which degrade to fugitive (i.e., gaseous) components on firing.

Organic solvents miscible with water can also be added. Examples of such organic solvents include acetone, methyl ethyl ketone, methanol, ethanol, and other alcohols and ketones. The presence of such solvents is useful when alteration of the viscosity of the dispersion is desirable provided they do not compromise the stability of the dispersion.

After a stable dispersion has been formed, it can be dried and shaped to form particles, fibers, flakes, or films, using techniques well known in the art. The stable dispersion can be solidified with, for example, urea-formaldehyde resin. The resin immobilizes the dispersion components and limits their subsequent segregation on firing. The resin is burned out on firing leaving a vestigial mass of powder of very fine particle size (less than about 1 micrometer) which can be readily deagglomerated with minimal mechanical grinding.

Although the dispersion can be dried by any method known to those skilled in the art, it is preferred to spray dry the dispersion to form a homogeneous, chemically pure powder using a conventional spray dryer. A suitable spray dryer can be set up so that a feed mixture is atomized (e.g., by passing through spray nozzles or a rotary wheel device) into a heated chamber. It is preferred that the chamber be heated to a suitable temperature so that sufficient water rapidly evaporates from the atomized dispersion droplets to produce a fine, free-flowing powder.

After drying, the powder is calcined by heating to a temperature sufficient to remove residual water, additives and solvents and to convert the salts present to the corresponding oxides. To do this efficiently, the powder is fed into a drop tower, fluidized bed heater, furnace or kiln.

The resultant calcined powder is fired, i.e., heated to sintering temperature. The sintering temperature is the temperature at which the oxides fuse to form an amorphous matrix from which leucite can be crystallized. The calcined powder can be fired in a standard kiln, but a rotary kiln is preferred for large quantities of powder. A variety of temperature profiles can be used. It has suprisingly been discovered that leucite may be crystallized at comparatively low temperatures, as low as 960° C. This is an unexpectedly low firing temperature when compared to conventional firing temperatures of greater than 1170° C. for leucite. The heat treatment affects the crystallite size and volume fraction of the leucite phase. Generally, fine grain sizes, i.e., less than 1 micrometer, are most desirable and can be obtained by using a fast ramp-up time and a brief heat soak at the sintering temperature. If desired, larger than 1 micrometer grain sizes can be obtained by prolonged heating times at sintering temperature.

Because the powder obtained by this process has a small particle size and a high degree of porosity, it is friable and generally intensive milling is unnecessary. However, if the particle size is larger than desired, the powder can be milled. The preferred milling methods are impact or impingement milling. Ball milling is less desirable because it tends to introduce impurities and debris from the milling media into the powder.

The fired and, optionally, milled leucite powder is examined by X-ray diffraction ("XRD") to verify that the powder consists of tetragonal leucite crystals. The XRD spectrum can be used to calculate the volume fraction of crystalline leucite.

Leucite powder is useful for mixing with components such as glasses and, if desired, opalescent-imparting components, fluorescent-imparting components and inorganic pigments to form compositions suitable for use as dental porcelains. It can also be used to form glass or glass-ceramic articles such as low melting glasses or electronic components.

For certain applications, dental porcelain may be pigmented to more closely match the coloration and appearance of natural dentition. Such pigmentation is generally accomplished by including small amounts of iron oxides and/or other inorganic oxides and pigments in the combination of frits which, on firing, matures into the final porcelain composition. However, the chemically derived leucite of this invention readily allows for incorporation of inorganic pigmenting or fluorescence-imparting agents directly in the leucite matrix by means of either particulates dispersed in the leucite precursor sol or as chemical constituents of the desired pigments dissolved in the leucite precursor sol which then develop into pigment particles on firing. Furthermore, this pigmentation or fluorescence can be accomplished with no adverse effect on the sol stability, the crystallization of leucite from the amorphous precursor matrix or the CTE of the leucite.

A major advantage to the process of the invention is that low processing temperatures are adequate to produce the chemically derived leucite. Other advantages are that leucite produced by this method has extremely high purity and homogeneity. These factors lead to rapid crystallization kinetics which afford the formation of fine leucite grains dispersed uniformly in an amorphous matrix of the same chemical composition.

Chemically derived leucite of the invention provides a composition that can be produced economically from its chemical constituents in a dispersion and that can be used to adjust the properties of a porcelain to provide greater flexibility in both the porcelains themselves and in the metal copings and substrates which can be utilized in conjunction with those porcelains. For example, tetragonal leucite can be incorporated into a porcelain to provide a dental porcelain having a CTE of about $8\times10^{-6}/°$ C. to about $24\times10^{-6}/°$ C. which could be fired onto a coping having a CTE ranging from about $8\times10^{-6}/°$ C. to about $20\times10^{-6}/°$ C. Preferably, the resultant dental porcelain has a CTE of about $9\times10^{-6}/°$ C. to about $16\times10^{-6}/°$ C.

The translucency and CTE, as well as other properties of dental porcelains, can be adjusted using the chemically derived leucite of the invention. Moreover, chemically pure tetragonal leucite can be used to provide increased flexibility in terms of the incorporation and quantity of the other components in a dental porcelain. Since pure tetragonal leucite can be obtained with this invention, porcelains can now be fabricated using low CTE, high strength glasses. Such porcelains may exhibit advantageous mechanical and/ or aesthetic properties heretofore unattainable.

The composition for forming the chemically derived leucite may optionally comprise additional components suitable for incorporation into porcelains. It is therefore possible to form a porcelain from a single frit.

The invention will be further clarified by a consideration of the following non-limiting examples, which are intended to be purely exemplary of the invention. All parts and percentages are by weight unless otherwise indicated.

PREPARATORY EXAMPLE

A 50% solution of potassium acetate was prepared by dissolving 2.52 kg of reagent grade CHCOOK (J. T. Baker Inc., Phillipsburg, N.J.) in 2.4 kg deionized water to which 120 g of reagent grade glacial acetic acid (J. T. Baker Inc., Phillipsburg, N.J.) had been added. The pH of the resultant solution was 7.6. The solution was vacuum filtered through a 0.22 micrometer pore size Millipore™ membrane (Millipore Corp., Bedford, Mass.) to remove insoluble contaminants.

An aqueous AFA solution was prepared by charging a 1 liter flask with 400 g of deionized water, 34.5 mL of glacial acetic acid and 25.6 mL of concentrated formic acid. The solution was brought to a rolling boil and 26.98 g of aluminum metal powder were added to the boiling carboxylic acid mixture in 3 portions of roughly 9 g each over a 2 hour period. An exothermic reaction ensued after the initial addition, and the rate of the reaction was moderated by the addition of room temperature deionized water. The digestion was continued for 10 hours, the solution was cooled and filtered. The solution contained 9.25% $Al_2O_3$ and had a pH of 4.45.

A silica sol commercially available as Nalco 1034A (Nalco Chemical Co., Inc., Naperville, Ill.) was used as obtained from the manufacturer. The sol was weakly turbid, suggesting the presence of aggregated particles somewhat larger than the 20 nanometer primary particle size specified by the manufacturer. The pH was measured and determined to be less than 4.0.

EXAMPLE 1

A 800 mL beaker fitted with a stirring bar was charged with 90 g of the acidified potassium acetate solution. AFA solution (253 g) was added with moderate stirring. The stirring frequency was increased and 162 g of silica sol was rapidly added. A foam layer formed due to entrainment of air in the mixture. The foam layer subsided within approximately 15 minutes to reveal a weakly turbid, blue-white colloid. The final dispersion, having a molar and weight % composition corresponding to leucite ($K_2OAl_2O_34SiO_2$), contained approximately 19.8% solids.

The above prepared dispersion was spray dried using a Buchi/Brinkmann Mini Spray Dryer (Model 190, Brinkmann Instruments Co., Division of Sybron Corporation, Westbury, N.Y.). The spray dryer outlet temperature was held at about 95°–105° C. The dispersion was stable and remained homogeneous throughout the run with no stirring required as the dispersion was pumped into the spray nozzle.

A white, flowable powder was collected from the cyclone discharge. The powder was put in a small alumina crucible and placed in an electric Ney Box Furnace (Model 2–525, The J. M. Ney Company, Bloomfield, Conn.) and heated to 1050° C. by increasing the temperature 20° C./min. The temperature was held at 1050° C. for 9.9 hours, then allowed to cool to 700° C. by decreasing the temperature 2° C./min. The temperature was held at 700° C. for 3 hours. The powder was removed from the 700° C. furnace and allowed to rapidly cool to room temperature (about 5 minutes).

The powder was examined by XRD. The XRD pattern indicated that the powder consisted of crystallographically pure tetragonal leucite.

EXAMPLE 2

A leucite precursor dispersion was prepared in four separate lots, each comprising approximately 9.5 liters. Each lot was prepared by charging a 19 liter vessel, fitted with a paddle stirrer, with 1.8 kg of acidified potassium acetate solution (equivalent to 432 g $K_2O$) and adding 5.06 kg of AFA solution (equivalent to 468 g $Al_2O_3$) with moderate agitation. This was followed by rapid addition (i.e., in approximately 1 minute) of 3.24 kg of the silica sol (equivalent to 1.10 kg $SiO_2$) with intense agitation to assure complete mixing and avoidance of concentration gradients. A foam layer formed and abated as described in EXAMPLE 1. The appearance and stability of the sol were as noted in EXAMPLE 1.

The separately prepared sol lots were combined and processed in a 0.91 meter diameter Mobile Minor Spray Dryer (Basic Model, Niro Inc., Columbia, Md.). The dispersion was sprayed using a 24 hole wheel atomizer run at approximately 29,000 rpm. The drying conditions were set at 290° C. inlet, 145° C. outlet, and 80 degree baffle angle. The drying and powder collection resulted in about 6.2 kg of powder.

Samples of the powder were fired in a Harper Single Door Box Kiln (Model HS-15182-K-28-F, Harper Electric Furnace Corp., Lancaster, N.Y.) at a variety of temperature profiles. The fired powder was examined by XRD to verify that the powder consisted of tetragonal leucite crystals. The XRD spectrum was used to calculate the volume fraction of crystalline leucite.

The CTE of each composition was determined by making a slurry (using distilled water) of each final composition and placing the slurry in a silicone mold to form a disk that was 4 mm in diameter and 6 mm thick. Three or four disks of each composition were prepared and fired in a porcelain furnace (Ultramat CDF, 3M Unitek, Irvine, Calif.) to 1100° C. at 55° C./min. Each disk was subjected to analysis using a thermal mechanical analyzer (Seiko SSC5200 TMA320) run at 25° C./min up to the softening temperature. The averaged CTE value for each composition was reported.

Set out in TABLE I are the run no., the thermal history, the % volume fraction of leucite (from XRD) and the CTE of the final composition.

TABLE I

| Run No. | Thermal History (Firing Profile) | % Volume Fraction (Vc) | CTE (×10⁻⁶/°C.) ±0.5 |
|---|---|---|---|
| 1 | 20° C./min → 1000° C. (10 hr) → 5° C./min → 500° C. (5 hr) → Q | 7 ± 1 | 10.2 |
| 2 | 20° C./min → 1050° C. (10 hr) → 2° C./min → 700° C. (3 hr) → Q | 36 ± 4 | 24.2 |
| 3 | 3 hr → 1000° C. (1 hr) → 8 hr | 11 ± 2 | 9.5 |
| 4 | 3 hr → 1000° C. (6 hr) → 8 hr | 94 ± 5 | 16.3 |
| 5 | 3 hr → 1200° C. (1 hr) → 8 hr | 96 ± 8 | 14.7 |
| 6 | 3 hr → 1200° C. (6 hr) → 8 hr | 100 ± 4 | 14.3 |
| 7 | 0 hr → 1000° C. (48 hr) → Q | 100 ± 2 | 26.4 |
| 8 | 0 hr → 1000° C. (6 hr) → Q | nm | 19.2 |
| 9 | 0 hr → 1000° C. (6 hr) → 6 hr | nm | 19.3 |
| 10 | 3 hr → 1000° C. (1 hr) → 6 hr | nm | 10.1 |
| 11 | 3 hr → 1000° C. (1 hr) → Q | nm | 12.3 |
| 12 | 0 hr → 1000° C. (1 hr) → Q | nm | 18.1 |
| 13 | 0 hr → 1100° C. (1 hr) → Q | nm | 18.8 |
| 14 | 0 hr → 1100° C. (6 hr) → Q | nm | 17.4 |
| 15 | 0 hr → 1100° C. (1 hr) → 6 hr | nm | 17.9 |

Q = Quench cooling
nm = Not measured

The data in TABLE I show that the volume fraction of tetragonal leucite congruently crystallized from the precursor powder depended on both the firing temperature and the amount of time the sample was maintained at the firing temperature. The CTE of many of the chemically derived leucite samples, especially Run Nos. 2, 7–9 and 12–13, was significantly greater than the CTE of leucite derived from feldspathic minerals by the conventional thermal processing route.

EXAMPLE 3

Five dispersions with varying amounts of aluminum nitrate substituted for some or all of the AFA alumina source were prepared according to the procedure of EXAMPLE 1. A 50% aluminum nitrate solution was prepared by dissolving 250 g $Al(NO_3)_3 \cdot 9H_2O$ crystals (Analytical Reagent, Mallinckrodt, Inc., Paris, Ky.) in 250 g deionized water. This solution was vacuum filtered through a 0.22 micrometer pore size membrane filter (Millipore, Inc., Bedford, Mass.) to remove suspended impurities. The 50% aluminum nitrate solution (equivalent to 6.79% $Al_2O_3$) was added to the AFA solution (equivalent to 9.25% $Al_2O_3$) contained in a 100 mL beaker in the weight ratios indicated in TABLE II. In each run, the AFA solution:$Al(NO_3)_3$ solution was equivalent to 2.34 g $Al_2O_3$ as fired solids. For each run, 16.2 g Nalco 1042 silica sol were gradually added with rapid stirring to the AFA solution:$Al(NO_3)_3$ solution. Nine grams of a 50% acidified potassium acetate solution were then gradually added to the silica:AFA:$Al(NO_3)_3$ sol with rapid stirring. The final equivalent oxide composition of each sample was 55.1% $SiO_2$, 23.4% $Al_2O_3$ and 21.6% $K_2O$, the exact stoichiometry of leucite. Each resultant dispersion was similar in appearance, exhibiting a blue-white translucency.

Set out in TABLE II are the run no., the amount (in grams) of AFA solution:$Al(NO_3)_3$ solution in the dispersion and the % of $Al_2O_3$ in the final solid derived from AFA:Al $(NO_3)_3$.

TABLE II

| Run No. | Amount AFA solution: $Al(NO_3)_3$ solution (g) | $Al_2O_3$ in Final Solid Derived from AFA: $Al(NO_3)_3$ (%) |
|---|---|---|
| 1 | 18.97:8.62 | 75:25 |
| 2 | 12.65:17.23 | 50:50 |
| 3 | 6.32:25.85 | 25:75 |
| 4 | 2.53:31.02 | 10:90 |
| 5 | 0:34.46 | 0:100 |

The five prepared dispersions were allowed to stand undisturbed at room temperature. Upon visual inspection at 14 days, the dispersions of Run Nos. 1 and 2 showed almost no change in turbidity and Run Nos. 3–5 exhibited a slight to moderate increase in turbidity.

EXAMPLE 4

Various additives were independently incorporated into 50 g aliquots of leucite precursor dispersion prepared as described in EXAMPLE 1. Each aliquot contained approximately 9.9 g leucite as final fired solids.

Set out in TABLE III are the run no., the source of each additive and the amount of each additive. For Run Nos. 1–5, the additive was gradually added to the leucite precursor dispersion with rapid stirring. For Run Nos. 6–7, the additive was added dropwise to the leucite precursor dispersion with rapid stirring.

TABLE III

| Run No. | Additive | Amount (g) |
|---|---|---|
| 1 | Reagent absolute alcohol[1] (95:5 vol. % ethanol:isopropanol) | 12.5 |
| 2 | N-methyl-2-pyrrolidone[2] Chrom AR-HPLC grade reagent | 12.5 |
| 3 | Dimethyl sulfoxide[3] (B&J brand high purity solvent) | 10.0 |

TABLE III-continued

| Run No. | Additive | Amount (g) |
|---|---|---|
| 4 | Polyglycol E200, polyethylene glycol[4] | 10.0 |
| 5 | Acrylic acid[5] | 8.8 |
| 6 | Triton X-405 nonionic surface active agent[6] (octylphenoxy polyethoxy ethanol) | 0.65 |
| 7 | Tween 80 nonionic surface active agent[7] (polyoxyethylene(20)sorbitan monooleate | 0.65 |

[1]Mallinckrodt Specialty Chemicals Co., Paris, NY
[2]Mallinckrodt Specialty Chemicals Co., Paris, NY
[3]American Burdick and Jackson, American Hospital Supply Corp., Muskegon, MI
[4]Dow Chemical Co., Texas Operations, Freeport, TX
[5]Aldrich Chemical Company, Inc., Milwaukee, WI
[6]Rohm and Haas, Inc., Philadelphia, PA
[7]ICI Americas, Inc., Wilmington, DE For Run Nos. 1–4 and 6–7, no visible changes in appearance (i.e., stability) were observed compared to the dispersion of EXAMPLE 1. For Run No. 5, no visible changes in appearance (i.e., stability) were observed immediately after mixing when compared to the dispersion of EXAMPLE 1. However, within approximately two hours after the addition of the acrylic acid, the modified dispersion became an opaque white gel. Even after eight weeks, the dispersions of Run Nos. 1–4 and 6–7 exhibited no visible changes in appearance compared to the dispersion of EXAMPLE 1.

EXAMPLE 5

A leucite precursor sol was prepared according to the procedure detailed in EXAMPLE 1. Urea (48.05 g, Certified ACS grade, Fisher Scientific Co., Fair Lawn, N.J.) was dissolved in a 200 mL aliquot (approximately 235 g) of leucite precursor sol to provide a 4M urea concentration. The dissolution reaction was endothermic, resulting in considerable cooling of the sol. The sol was allowed to warm to room temperature, at which time 120 mL (about 127 g) of a 37% aqueous solution of formaldehyde (Reagent grade, J. T. Baker Chemical Co., Phillipsburg, N.J.) was added with rapid stirring. The urea-formaldehyde molar ratio of the mixture was about 1:2 and the leucite solids content (as oxide solids) was about 11.5%.

Concentrated nitric acid (10 mL) was added to a 100 mL aliquot of the leucite precursor sol:urea-formaldehyde mixture with rapid stirring. Immediately after the addition of the nitric acid to catalyze polymerization of the urea-formaldehyde resin, an opaque white, highly viscous gel formed which solidified in a few minutes to a rigid white opaque block of resin. The rapid onset of high viscosity and solidification ensured that the leucite precursor sol retained its homogeneous composition despite its incorporation into the urea-formaldehyde polymer mass.

The resin block was removed by breaking the beaker in which it was cast. The block was flash fired in an alumina crucible in a Ney oven (Model no. 2-525, The J. M. Ney Company, Bloomfield, Conn.) at 1000° C. for 30 minutes. Upon removal from the oven, the sample consisted of a fragile mass of white powder which readily disintegrated on handling.

The absence of any grey color or black carbon specks in the resultant powder indicated that the resin and all its combustion byproducts were cleanly and completely removed from the leucite precursor on firing. A scanning electron micrograph ("SEM") of the powder showed the uniform fine structure of the leucite powder; whereas, SEM of a ball milled sample of a commercially available porcelain powder showed non-uniform angular particles.

EXAMPLE 6

Pigmented leucite was prepared by the independent addition of solutions of ferric nitrate, alpha-FeOOH (goethite) and chromium nitrate to leucite precursor sols. For each pigmented leucite precursor sol, both the AFA solution and the acidified potassium acetate solution were prepared according to the procedure outlined in the PREPARATORY EXAMPLE.

An iron-doped leucite precursor sol was prepared by adding to 303.6 g of AFA solution 5.0 mL of a 3M aqueous ferric nitrate solution prepared from reagent grade $Fe(NO_3)_3 9H_2O$ (Mallinckrodt, Inc., Paris, Ky.) which was vacuum filtered through a 0.22 micrometer pore size membrane filter (Millipore, Inc., Bedford, Mass.) to remove suspended impurities. Nalco 1042 silica sol (194.4 g) was added to the wine-red AFA:ferric nitrate solution with rapid stirring. Then 108.0 g of 50% aqueous acidified potassium acetate solution was added to the AFA:ferric nitrate:silica sol, resulting in the formation of a stable, weakly turbid, translucent red-brown sol.

Another iron-doped leucite precursor sol was prepared as detailed above, except that 20.0 g of an aqueous dispersion of alpha-FeOOH containing 6.1% FeOOH was used instead of the ferric nitrate solution. The alpha-FeOOH was prepared in a manner similar to Example 1 of U.S. Pat. No. 4,873,010. The resulting leucite precursor sol was opaque and yellow-brown in color.

A chromium-doped leucite precursor sol was prepared as described for the preparation of the ferric nitrate iron-doped leucite precursor sol, except that 6.0 mL of 2.5M $Cr(NO_3)_3$ was used instead of the $Fe(NO_3)_3$ solution. The chromium nitrate solution was prepared from reagent grade $Cr(NO_3)_3 9H_2O$ (Fisher Scientific Co., Fair Lawn, N.J.) and vacuum filtered through a 0.22 micrometer pore size membrane filter (Millipore, Inc., Bedford, Mass.) to remove suspended impurities. The resultant solution was weakly turbid, translucent and purple-red in color.

The composition of each of the above prepared samples, calculated on the basis of the equivalent metal oxide content after firing, was that of stoichiometric leucite plus approximately 1.1% pigment as either $Fe_2O_3$ or $Cr_2O_3$.

Each sol sample was independently spray dried as described in EXAMPLE 1. The resultant powders were faintly tinted due to the presence of either iron or chromium.

Ten grams of each of the spray dried samples was spread in a thin layer in a 5.08 cm×10.16 cm alumina crucible. Each sample was then placed in a box furnace (Lindberg, Inc., Watertown, Wis.) equipped with a single zone temperature controller (Series 2010, Applied Test Systems, Inc., Butler, Pa.). The firing temperature was raised from room temperature to 1000° C. in 5 hours, soaked at 1000° C. for 3 hours and then allowed to cool to room temperature with no controlled ramp.

Approximately 6.5 g of lightly caked powder was recovered from each crucible. The powders made using ferric nitrate solution, alpha-FeOOH sol and chromium nitrate solution were light orange, orange and pale yellow respectively. The pigmentation was not uniform throughout the powder mass, but was less intense at the upper surface of the powder compared to the lower surface of the powder in contact with the alumina crucible.

EXAMPLE 7

A high potassia leucite (i.e., kalsilite) precursor sol was prepared by gradually adding 2.88 kg Nalco 1042 silica sol (equivalent to 34.0% silica) to 4.54 kg AFA solution (equivalent to 9.25% alumina) with rapid stirring. Then 2.50 kg 50% aqueous acidified potassium acetate solution (equivalent to 24.0% potassia) was gradually added to the silica sol:AFA mixture with rapid stirring. The resulting stable weakly turbid sol exhibited a blue-white translucency. The equivalent solids composition of the sol was 49.0% $SiO_2$, 21.0% $Al_2O_3$ and 30.0% $K_2O$.

The resultant sol was spray dried according to the procedure detailed in EXAMPLE 2. The sol feed rate to the atomizer was maintained at about 25 cm$^3$/minute. The collected kalsilite powder was white and free flowing.

Samples of the kalsilite powder were fired in the Harper Kiln described in EXAMPLE 2 at a variety of temperature profiles. Crystallization of the high CTE phases of kalsilite and kaliophyllite (both $KAlSiO_4$ polymorphs) and/or leucite occurred in varying proportions depending on the firing profile.

Set out in TABLE IV are the run no., the thermal history, the ratio of kalsilite:leucite produced (based on XRD) and the CTE of the final composition. The CTE values were obtained by thermal mechanical analysis as detailed in EXAMPLE 2. Each run was the average of two samples.

TABLE IV

| Run No. | Thermal History (Firing Profile) | Ratio of Kasilite: Leucite | CTE (×10$^{-6}$/°C.) ±0.5 |
|---|---|---|---|
| 1 | 3 hr → 1000° C. (1 hr) → Q | 100:0 | 17.3 |
| 2 | 3 hr → 1000° C. (6 hr) → Q | 100:28 | 16.2 |
| 3 | 3 hr → 1100° C. (3.5 hr) → Q | 100:33 | 17.4 |
| 4 | 3 hr → 1100° C. (3.5 hr) → Q | 100:38 | 16.1 |
| 5 | 3 hr → 1200° C. (1 hr) → Q | 100:21 | 16.0 |
| 6 | 3 hr → 1200° C. (6 hr) → Q | 100:43 | 16.3 |

Q=Quench cooling

The data in TABLE IV show that pure kalsilite can be obtained using the firing profile of Run No. 1. At either longer soak times at 1000° C. (Run No. 2) or soak temperatures >1000° C. (Run Nos. 3–6) XRD results indicate that significant amounts of leucite are present along with the kalsilite phase. The high CTE exhibited by the pure kalsilite phase produced in Run No. 1 is equivalent to or greater than the CTE of the kalsilite:leucite mixtures produced under the other firing profiles listed in TABLE IV. Any of the powders produced under the conditions listed in TABLE IV would be suitable for incorporation into dental porcelains as the high expansion phase.

EXAMPLE 8

A porcelain fused to metal crown restoration was prepared on a low CTE coping and a porcelain fused to metal bridge was prepared on a high CTE coping using a dental porcelain containing chemically derived tetragonal leucite.

Approximately 5 g of porcelain powder was prepared by combining 90% alkali aluminosilicate glass (CGW 0080, Corning Inc., Corning, N.Y.) and 10% chemically derived leucite of EXAMPLE 1. The components were ground and mixed in a mortar and pestle until a very fine powder was obtained. Distilled water (3–5 drops) was added to the porcelain powder and the blend was mixed to a creamy consistency.

A standard lost wax process was used to form a single unit coping (i.e., a crown) from a chromium-nickle-molybdenum alloy (CTE of 13.8–14.2×10$^{-6}$/° C., Forte™, Teledyne Allrac, Monroe, N.C.) and a three unit bridge from a high silver-palladium alloy (CTE of 15.6×10$^{-6}$/° C.,) 37 5% silver–53% palladium, Celebrity™, Wilkenson Gold, 1000 Oaks, Calif.). A layer of opaque porcelain (Vintage™, 3M) was fired at 960° C. on the surface of both copings.

The above prepared porcelain slurry was independently applied to the fired opaque layer of each coping at a thickness of about 0.5 mm and blotted with a paper towel. The restorations were then fired in a porcelain furnace (Ultramat CDF, 3M Unitek, Irvine, Calif.).

The first firing in vacuum was made by placing the restorations in the furnace at 650° C. and in 10 minutes increasing the temperature to 810° C. at 55° C. per minute. After a hold time of 1 minute at 810° C., the restorations were removed from the furnace, anatomy was carved into them and additional porcelain slurry was added. The restorations were then subjected to a second firing regimen identical to the first firing.

The restorations were removed from the furnace, more detailed anatomy was carved into them and they were then polished. A glaze was applied to each restoration before being subjected to a third firing. The third firing was identical to the first and second firings, except that in 3 minutes (instead of 10 minutes) after placement in the furnace at 650° C., the temperature was increased to 800° C. After removal from the furnace, the restorations were polished.

Both restorations were uncracked and exhibited excellent appearance. This shows that porcelain powders containing leucite of the invention are compatible with a wide range of alloys and can be fired at significantly lower temperatures than most commercial porcelains.

Porcelain prepared using the leucite of the invention may also be used for inlays, onlays, veneers and other dental restorations.

It is intended that the specification and examples be considered as exemplary only, with the true scope and spirit of the invention being indicated by the following claims.

What is claimed:

1. A process of making chemically derived leucite comprising the step of admixing a potassia precursor, an alumina precursor and a silica precursor to form a uniform suspension of finely divided particles in a liquid medium such that the particles are capable of remaining uniformly distributed throughout the spension for at least on hour a 25° C. from which a composition is formed having a dry weight solids content after firing on a theoretical basis of 12 to 30 weight % $K_2O$, 8 to 30 weight % $Al_2O_3$ and 45 to 73 weight % $SiO_2$; wherein said potassia precursor, alumina precursor and silica precursor are limited to salts, solutions derived from a salt, or sols from which a subsequent oxide composition is obtained.

2. The process of claim 1, wherein the dispersion is free of processing aids and transition metal cations.

3. The process of claim 1, further comprising an additive.

4. The process of claim 3, wherein said additive is a fiberizer.

5. The process of claim 3, wherein said additive is an organic solvent.

6. The process of claim 5, wherein said organic solvent is selected from the group consisting of acetone, methyl ethyl ketone, methanol and ethanol.

7. The process of claim 3, wherein said additive is a drying control additive.

8. The process of claim 3, wherein said additive is a film forming agent.

9. The process of claim 3, wherein said additive is a surfactant.

10. The process of claim 3, wherein said additive s a plasticizer.

11. The process of claim 3, wherein said additive is a monomer.

12. The process of claim 3, wherein said additive is a polymer.

13. The process of claim 1, further comprising the addition of a resin in said dispersion so that the dispersion may be solidified before firing, thereby immobilizing dispersion components.

14. The process of claim 13, wherein said resin is urea-formaldehyde.

15. The process of claim 1, further comprising the steps of b) drying said dispersion to form a composition;

c) calcining said composition formed by step b); and d) firing said composition formed by step c).

16. The process of claim 15, wherein the composition formed by step d) comprises a crystalline phase and an amorphous phase, said crystalline phase comprising tetragonal leucite, such that the amorphous phase has the same stoichiometric composition as the crystalline phase.

17. The process of claim 16, wherein the tetragonal leucite after firing consists essentially of 21.6 weight % $K_2O$, 23.4 weight % $Al_2O_3$ and 55.0 weight % $SiO_2$.

18. The process of claim 17, wherein said composition consists essentially of tetragonal leucite wherein the amorphous phase has the same stoichiometric composition as the crystalline phase.

19. The process of claim 15, further comprising the step of formulating a dental porcelain comprising said composition formed by step d).

20. The process of claim 19, wherein said porcelain is derived from a single frit.

21. The process of claim 19, wherein said porcelain has a CTE of about $8 \times 10^{-6}/°$ C. to about $24 \times 10^{-6}/°$ C.

22. The process of claim 19, wherein said porcelain has a CTE of about $9 \times 10^{-6}/°$ C. to about $16 \times 10^{-6}/°$ C.

23. The process of claim 21, wherein the porcelain is fired onto a coping, said coping having a CTE of about $8 \times 10^{-6}/°$ C. to about $20 \times 10^{-6}/°$ C.

24. The process of claim 1, further comprising one or more metals selected from the group consisting of alkali, alkaline, transition and rare earth metals in an amount from 0.1 to 20 weight %.

25. The process of claim 1, further comprising a fluorescent agent.

26. The process of claim 1, further comprising a pigment.

27. The process of claim 1, wherein said dispersion has a pH less than 7.

28. The process of claim 1, wherein said dispersion has a pH of 3–6.

29. The process of claim 1, wherein said dispersion has a pH of 5–6.

30. The process of claim 1, wherein said dispersion has a total dry weight solids content after firing of no more than 20.2 weight %.

31. The process of claim 1, wherein said dispersion has a total dry weight solids content after firing of no more than 19.8 weight %.

32. The process of claim 1, wherein at least 40% of the theoretical maximum yield of leucite is crystallized.

33. The process of claim 1, wherein at least 75% of the theoretical maximum yield of leucite is crystallized.

34. The process of claim 1, wherein at least of the 95% of the theoretical maximum yield of leucite is crystallized.

35. The process of claim 1, wherein the potassia precursor comprises potassium acetate.

36. The process of claim 1, wherein the alumina precursor comprises aluminum formoacetate.

37. The process of claim 1, wherein the silica precursor comprises an aqueous silica sol.

* * * * *